(12) United States Patent
Kugler et al.

(10) Patent No.: US 6,627,130 B2
(45) Date of Patent: Sep. 30, 2003

(54) METHOD AND APPARATUS FOR GEOMETRIC SCARFING

(75) Inventors: Joseph Michael Kugler, Appleton, WI (US); Michael Barth Venturino, Appleton, WI (US); Todd Christy Thoman, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 372 days.

(21) Appl. No.: 09/840,384

(22) Filed: Apr. 23, 2001

(65) Prior Publication Data
US 2002/0153634 A1 Oct. 24, 2002

(51) Int. Cl.⁷ .............................. A61F 13/15; B27N 3/00
(52) U.S. Cl. ...................... 264/118; 264/518; 264/121; 425/83.1
(58) Field of Search ................. 264/118, 121, 264/518; 425/83.1

(56) References Cited

U.S. PATENT DOCUMENTS

| | | |
|---|---|---|
| 4,495,119 A | 1/1985 | Chung |
| 4,592,708 A | 6/1986 | Feist et al. |
| 4,626,184 A | 12/1986 | Hammond |
| 4,666,647 A | 5/1987 | Enloe et al. |
| 4,675,144 A | 6/1987 | Hammond |
| 4,690,853 A | 9/1987 | Hammond |
| 4,761,258 A | 8/1988 | Enloe |
| 4,859,388 A | 8/1989 | Peterson et al. |
| 4,927,582 A | 5/1990 | Bryson |
| 4,971,852 A | 11/1990 | Hammond |
| 5,288,220 A | 2/1994 | Kugler et al. |
| 5,427,723 A | 6/1995 | Kugler et al. |
| 5,447,667 A | 9/1995 | Masson |
| 5,772,813 A | 6/1998 | Bitowft et al. |

FOREIGN PATENT DOCUMENTS

| | | |
|---|---|---|
| EP | 0 155 752 B1 | 1/1985 |
| EP | 0 627 211 B1 | 6/1994 |
| EP | 0 627 211 A1 | 6/1994 |
| WO | WO 85/04366 | 10/1985 |

Primary Examiner—Mary Lynn Theisen
(74) Attorney, Agent, or Firm—Paul Y. Yee

(57) ABSTRACT

A method and apparatus (20) for scarfing a fibrous web (22) can include a scarfing housing (24) which has been provided with a web entrance portion (26), a web exit portion (28), a discharge conduit (30), and an air flow inlet (32, 54). A rotatable scarfing roll (34) can be located in the scarfing housing (24), and in a particular feature, the discharge conduit (30) can be configured with a distinctive conduit angle (36).

20 Claims, 9 Drawing Sheets

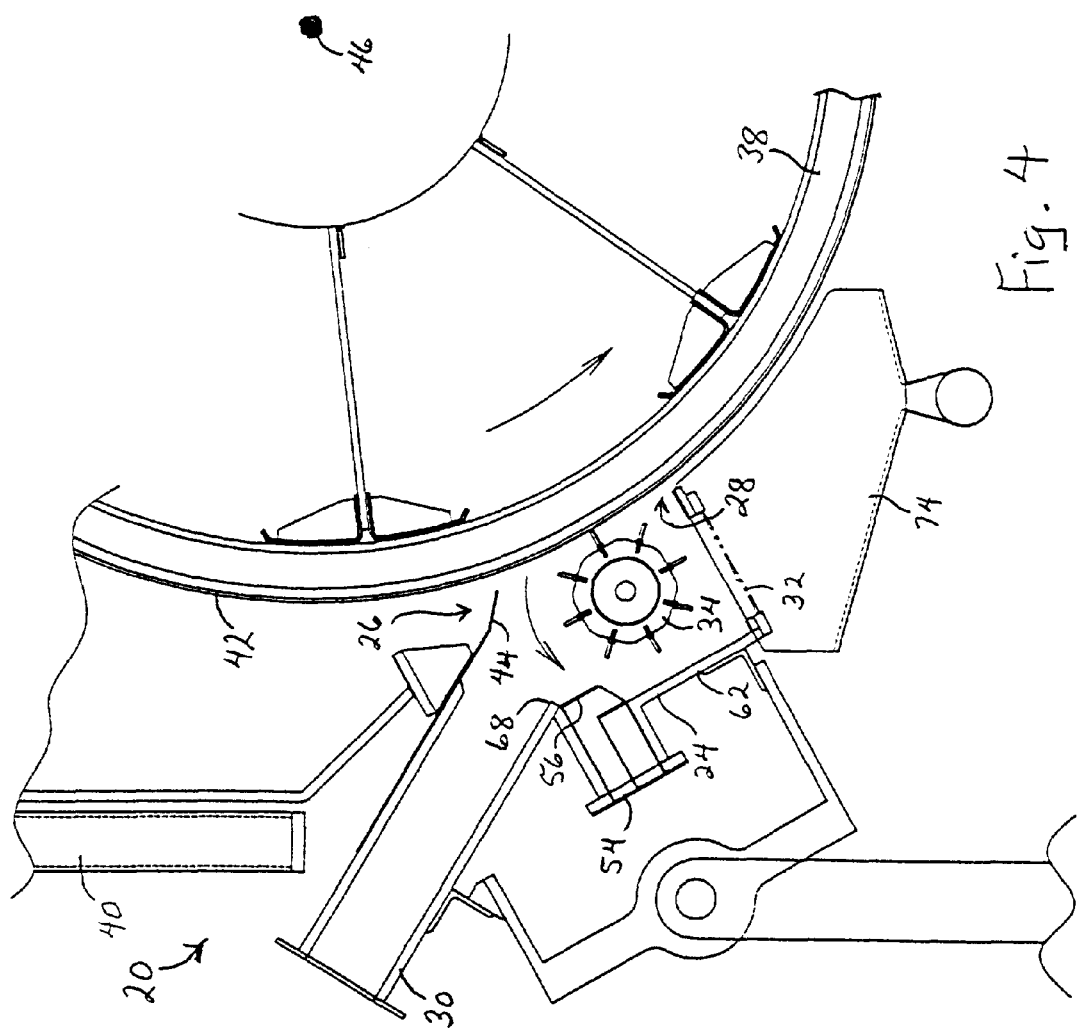
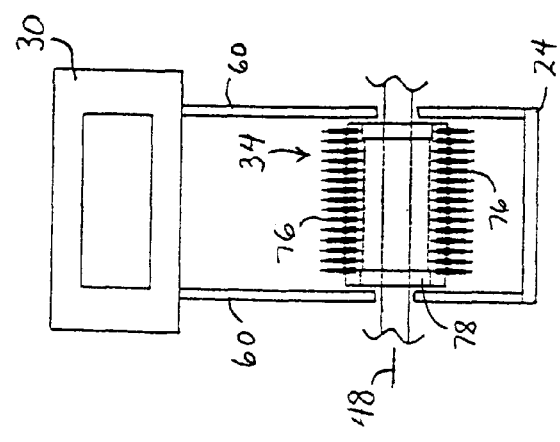
Fig. 4
Fig. 4A

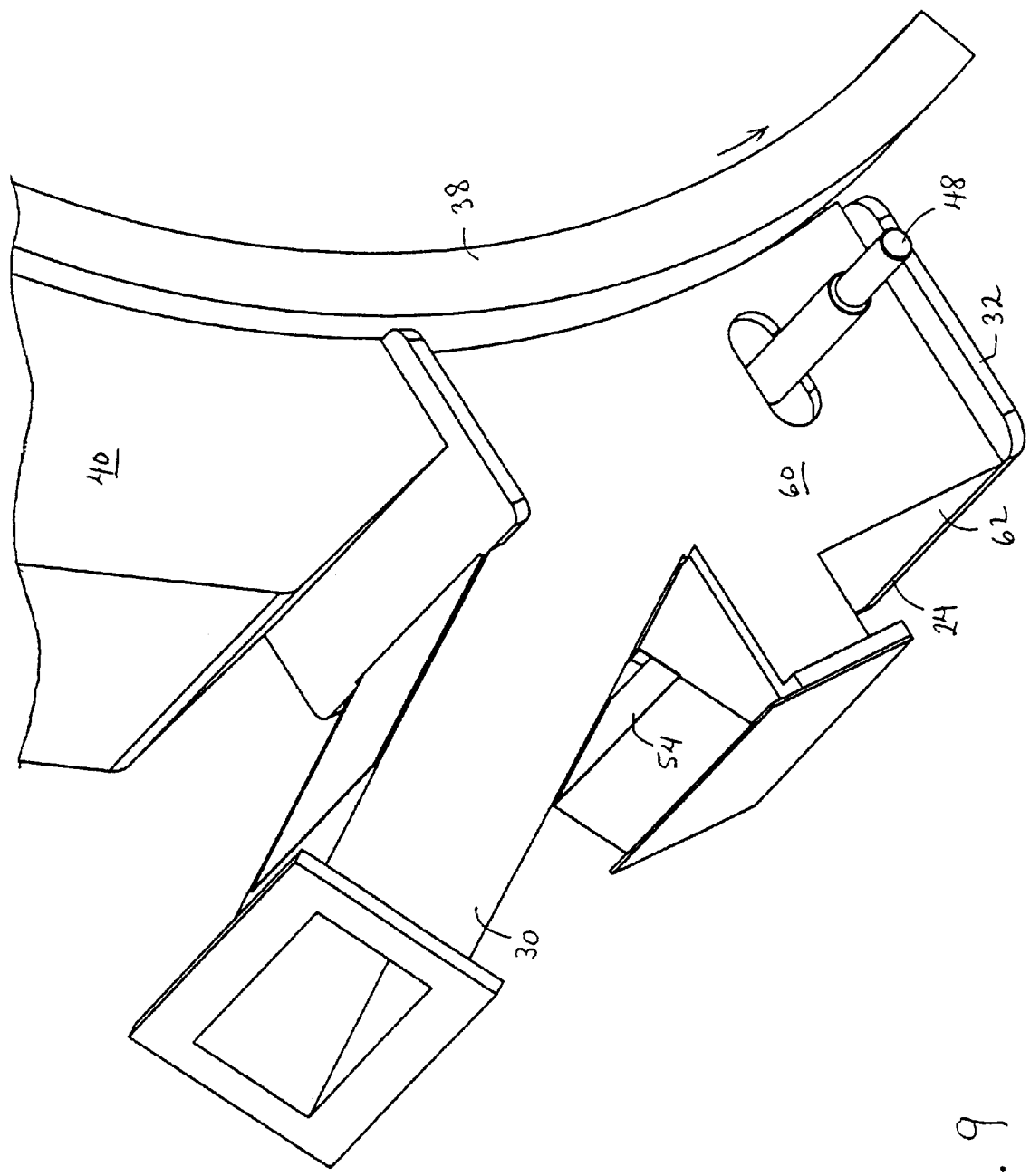

METHOD AND APPARATUS FOR GEOMETRIC SCARFING

FIELD OF THE INVENTION

This invention generally relates to apparatus and method for forming a fibrous article. The fibrous article can be a fibrous web, and the fibrous web may be employed to produce absorbent pads for applications such as disposable diapers, child's training pants, feminine care articles, incontinence articles, and the like.

BACKGROUND OF THE INVENTION

In the general practice of forming fibrous web materials, such as laid fibrous articles, it has been common to utilize a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a foraminous forming surface upon which the fibers and superabsorbent particles have been deposited to form an absorbent fibrous web. Typically the formed fibrous web has provided an interconnected plurality of appointed, fibrous pads. The fibrous web has been cut or otherwise segmented to provide individual pads. During the manufacturing operations, the scarfing operation has been employed to provide multiple functions. For example, the scarfing operation has been employed to level the peaks and valleys off the top of the formed fibrous web so that, from pad to pad along the length of the fibrous web, each pad can have substantially the same basis weight of absorbent material. Additionally, the scarfing operation has been employed to help control and regulate the desired basis weight distributions within each individual pad.

Adjustments to the basis weight distributions have, for example, been made by providing a foraminous forming surface that has predetermined depressions or pocket regions that allow an accumulation of relatively large amounts of absorbent material. Additionally, the location and configuration of the scarfing roll has been selectively adjusted. For example, by reducing the effective gap between the scarfing roll and the forming surface, the scarfing roll can be arranged to remove more material from the fibrous web. The amounts of removed material have been recirculated through the forming process, and have been employed to help fill the deeper pocket regions of the forming surface. The filling of the pocket regions has been accomplished by an over-forming of the pad with the selected absorbent material, and a mechanical redistribution of the absorbent material.

The prior practice of forming airlaid fibrous webs has employed various scarfing mechanisms to produce desired distributions of basis weight along the formed fibrous webs. For example, the scarfing mechanisms have been employed to produce gradations of basis weight along a longitudinal direction of the formed web, i.e., in the direction of movement of the fibrous web through the forming process or apparatus. Conventional scarfing mechanisms have also been employed for providing basis weight variations along a transverse, cross-direction of the formed web.

For example, particular scarfing systems have employed scarfing rolls that have been configured to provide a timed scarfing of the fibrous web. In other systems, a web conveyor is moved towards and away from the scarfing roll to generate changes in basis-weight distribution. Further systems have employed multiple scarfing rolls, or have employed a reverse venting airflow.

Absorbent pads in desired consumer products are, however, being constructed with relatively large differences in the amount of absorbent material placed in different sections of the pad. For example, larger amounts of absorbent fiber and superabsorbent particles are being placed in the appointed front portions of the pad, and much smaller amounts of absorbent fiber and superabsorbent particles are being placed in the appointed back portions of the pad. As a result, a basis-weight profile can be generated across the length and/or width of the pads, and the profiles can include large changes in basis-weight. The manufacture of such pads with high-variation, basis-weight profiles has required the scarfing of larger amounts of material at higher scarfing rates. Conventional scarfing systems, however, have not adequately provided the higher levels of scarfing mass-flow needed to produce the desired pads. Conventional scarfing systems, such as those described above, have experienced various difficulties. One difficulty has been an increased re-circulation of fibers from the scarfing housing back into the forming chamber. This situation can make it difficult to maintain a desired basis weight in the fibrous web. Another difficulty has been a plugging or jamming of the fibrous web as it leaves the forming chamber or as the fibrous web enters the scarfing housing. This situation can develop during transient situations, such as during a sequence of shutting down and starting up the web forming operation. In a further difficulty, the fibrous material that has been scarfed and removed from the fibrous web may not be adequately discharged from the scarfing housing. As a result, an accumulation of fibrous material may jam or otherwise degrade the scarfing operation. For example, fibrous material may accumulate within the scarfing housing and, at random intervals, break free to redeposit onto the fibrous web. The relatively unpredictable redeposit of fibrous material can generate excessive variations in the basis weight of the fibrous web. Where the fibrous web also includes particulate material, such as particles of superabsorbent material, the particulate material removed from the web may not be adequately directed out of the discharge conduit, and may accumulate within the scarfing housing, or may undesirably exit out from other openings in the scarfing housing. As a result, there has been a continuing need for improved scarfing systems that can more reliably produce and maintain the desired distributions of basis weight along the scarfed web.

BRIEF DESCRIPTION OF THE INVENTION

The present invention provides a distinctive method and apparatus for scarfing a fibrous web. The technique of the invention can include a scarfing housing which has been provided with a web entrance portion, a web exit portion, a discharge conduit, and an air flow inlet. A rotatable scarfing roll can be located in the scarfing housing, and the discharge conduit can be configured with a selected conduit angle. In a particular aspect, the discharge conduit can be configured with a conduit angle of not more than about 80 degrees.

In another aspect, the method and apparatus of the invention can include a movable damper which is operatively positioned in the web entrance portion of the scarfing housing, and is capable of changing a size of an entrance opening in the web entrance portion of the scarfing housing. In a further aspect, the method and apparatus of the invention can include an inlet chimney portion which is configured to provide a selected stripper air flow towards the scarfing roll. In still another aspect, the method and apparatus can include at least one insert member which is configured to operatively impede a movement of particulate material removed from the fibrous web during the scarfing of the fibrous web.

In its various aspects and features, the method and apparatus of the present invention can more effectively help to provide an improved technique for scarfing fibrous webs. The invention can provide a distinctive scarfing system which can exhibit a higher scarfing capacity, a decreased plugging tendency, and a reduced variability in the desired basis weight distributions that are intended for production along and across the scarfed web.

BRIEF DESCRIPTION OF THE DRAWINGS

The invention will be more fully understood and further advantages will become apparent when reference is made to the following detailed description of the invention and to the drawings in which:

FIG. 4 shows a schematic, cross-sectional side view of a representative method and apparatus of the present invention having an alternative inlet chimney and an alternative insert member;

FIG. 4A shows a partially sectioned, end view of the scarfing system that is representatively shown in FIG. 4;

FIG. 9. shows cut-away, perspective view of a representative apparatus and method of the invention.

DETAILED DESCRIPTION OF THE INVENTION

Figure 1:
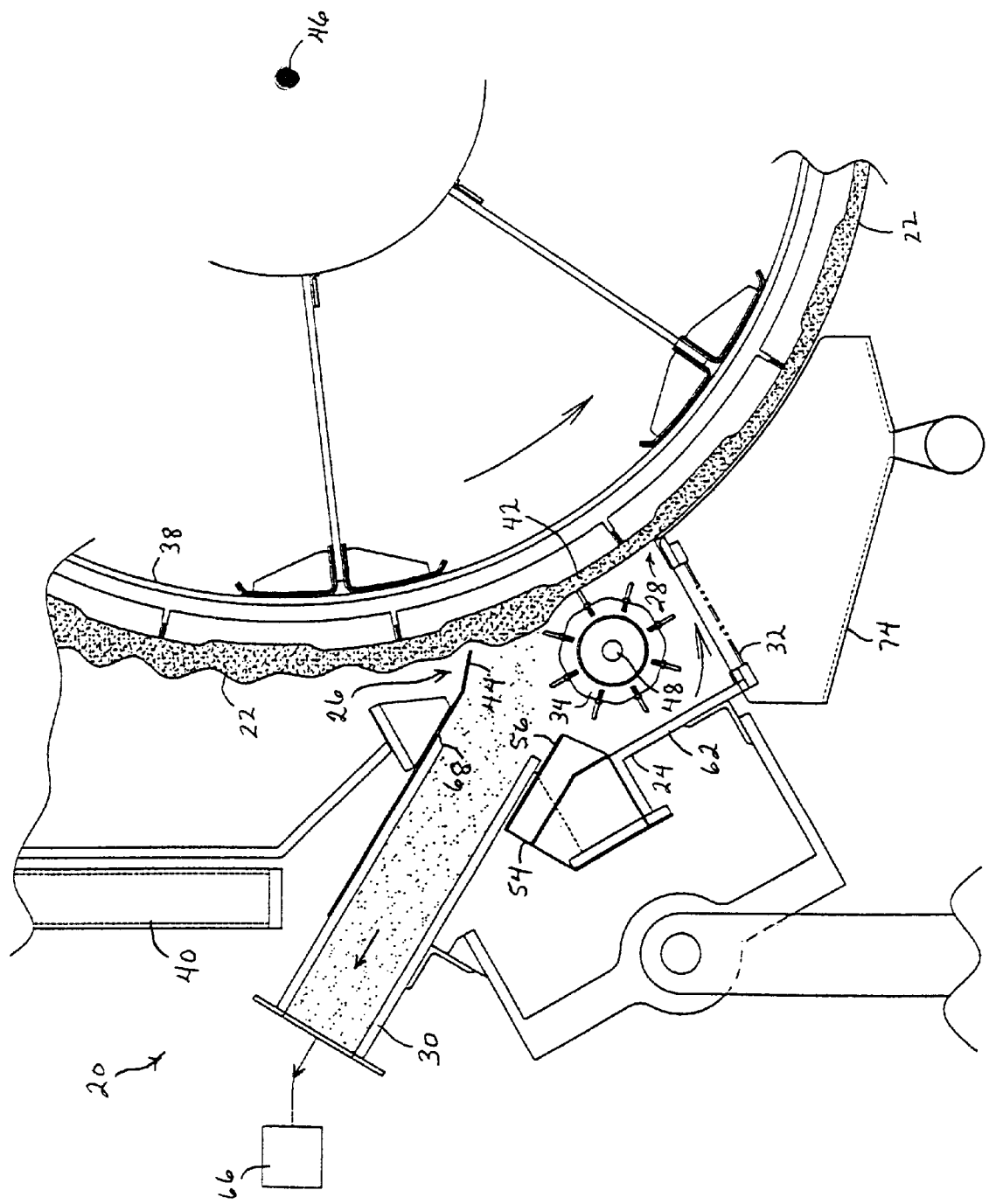
FIG. 1 shows a schematic, cross-sectional side view of a representative method and apparatus that incorporates the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

With reference to FIGS. 1, 2–2A, 8 and 9, a distinctive method and apparatus 20 for scarfing a fibrous web 22 can include a scarfing housing 24 which has been provided with a web entrance portion 26, a web exit portion 28, a discharge conduit 30, and an air flow inlet 32. A rotatable scarfing roll 34 can be located in the scarfing housing 24, and the discharge conduit 30 can be configured with a selected conduit angle 36 (e.g. FIG. 6). In a particular feature, the conduit angle can be not more than a maximum of about 80 degrees (80°). In a further feature, the conduit angle can be not more than a maximum of about 60 degrees (60°).

In another aspect, the method and apparatus can include a movable damper 44 which is operatively positioned in the web entrance portion 26 of the scarfing housing 24, and is capable of changing a size of an entrance opening in the web entrance portion 26 of the scarfing housing 24. In a further aspect, the method and apparatus can include an inlet chimney portion 54 which is configured to provide a selected stripper air flow towards the scarfing roll 34. In still another feature, the method and apparatus can include at least one insert member 56 which is configured to operatively impede a movement of particulate material removed from the fibrous web 22 during the scarfing of the fibrous web. Further features and aspects of the invention are set forth in the present disclosure.

As representatively shown, the method and apparatus 20 can include a forming chamber 40 and a transporter for moving a cooperating, foraminous forming surface 42 through the forming chamber. The fibrous web 22 is produced on the forming surface and the selected transporter can move the formed fibrous web out from the forming chamber 40 and into the scarfing housing 24. Additionally, the transporter can convey the fibrous web 22 through the scarfing housing 24 and out from the housing exit portion 28 for further processing. To provide desired air flows into and through the scarfing housing 24 and discharge conduit 30, a conventional air-moving system can be operatively connected to the discharge conduit 30. For example, a discharge fan 66 of suitable power and capacity can be connected to the discharge conduit. Such fans are well known in the art and are available from commercial vendors.

The method and apparatus of the present invention can be employed with any suitable fibrous web. The webs may be generated by various techniques, such as wet-forming techniques, foam forming techniques, airforming techniques or the like, as well as combinations thereof. Such webs may, for example, be airlaid, and may contain natural and/or synthetic fibers, as well as superabsorbent material (SAM). The superabsorbent material can be in particulate form. In particular arrangements, the absorbent fiber can include cellulosic woodpulp fluff.

Conventional scarfing systems have experienced various difficulties. One difficulty has been a recirculation of large amounts of fibers from the scarfing housing 24 back into the forming chamber 40. This situation can make it difficult to maintain a desired basis weight in the fibrous web 22. Another difficulty has been a plugging or jamming of the fibrous web 22 as it leaves the forming chamber 40 or as the fibrous web enters the scarfing housing 24. This situation can develop during transient situations, such as during a sequence of shutting down and starting up the web forming operation. In a further difficulty, the fibrous material that has been scarfed and removed from the fibrous web 22 may not be adequately discharged from the scarfing housing 24. As a result, an accumulation of fibrous material may jam or otherwise degrade the scarfing operation. For example, fibrous material may accumulate within the scarfing housing and, at random intervals, break free to redeposit onto the fibrous web 22. The relatively unpredictable redeposit of fibrous material can generate excessive variations in the basis weight of the fibrous web. Where the fibrous web also includes particulate material, such as particles of superabsorbent material, the particulate material removed from the web 22 may not be adequately directed out of the discharge conduit 30, and may accumulate within the scarfing housing 24, or may undesirably exit out from other openings in the scarfing housing. While suitable devices, such as the representatively shown catch-pan 74, may be employed to capture the fugitive particles, the monitoring and emptying of the catch-pan can excessively raise manufacturing costs.

By incorporating its various aspects and features, alone or in selected combination, the present invention can provide an improved method and apparatus for scarfing fibrous webs. The improved scarfing system of the invention can provide a higher scarfing capacity, can exhibit a decreased plugging tendency, and can generate a reduced variability in the desired basis weight distributions in the scarfed web. In a particular feature, the method and apparatus of the present invention can more effectively distribute the fibrous material, and can provide a more effective and reliable control of the desired basis weight along the lengthwise, machine-direction of the fibrous web 22.

In the illustrated arrangement, the transporter is provided by a rotatable forming drum 38. Alternatively, any other operative transporter mechanisms may be employed. For example, the transporter may be provided by an endless belt, which is operatively driven by a conventional power system in a manner known in the art to move the fibrous web 22 from the forming chamber 38 and through the scarfing housing 24.

In the representatively shown configuration, the forming drum 38 has a drum axis of rotation 46, and the forming drum is configured to rotate in a counter-clockwise direction. Optionally, the forming drum 38 may be configured to rotate in a clockwise direction.

Suitable forming drum systems for producing airlaid fibrous webs are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

The scarfing housing 24 is suitably constructed to provide a structure which can operatively enclose the fibrous web 22 during the scarfing operation. For example, the scarfing housing can include a wall member which provides the entrance portion 26, a wall member which provides the housing exit portion 28, housing side wall members 60 and a suitable housing cover wall member 62. The housing entrance portion 26 includes an entrance opening through which the fibrous web 22 enters the scarfing housing 24. The housing exit portion 28 includes an exit opening through which the fibrous web departs the scarfing housing 24 or further processing after the scarfing operation.

The scarfing roll 34 has an axis of rotation 48, and typically, the rotational axis 48 of the scarfing roll axis can be aligned substantially parallel to the rotational axis 46 of the forming drum. The scarfing roll axis and the drum axis may optionally be arranged to be non-parallel. Additionally, the scarfing roll can be positioned operatively adjacent the forming surface 42 provided by the forming drum 38, and the separation distance between the outer circumference of the scarfing roll 34 and the forming surface 42 can be selectively arranged to produce a desired thickness in the scarfed fibrous web.

Scarfing rolls are well known in the art, and any conventional scarfing roll may be employed with the present invention. Suitable scarfing rolls are available from the Paper Converting Machine Company, a business having offices located in Green Bay, Wis., U.S.A. and from Curt G. Joa, Incorporated a business having offices located in Sheboygan Falls, Wis., U.S.A.

In the illustrated configuration, for example, the scarfing roll 34 can include a plurality of scarfing pins or other scarfing elements 76 that are operatively mounted and attached to a core member 78. The scarfing roll core can, for example, be generally cylindrical, and can have a diameter of about 5 inch (about 13 cm). Additionally, the outer diameter of the scarfing roll at the distal tips of the scarfing pins or other scarfing elements can be within the range of about 6–10 inch (about 15–25 cm). The scarfing roll can have an axial length that is within the range of about 3–20 inch (about 7.6–51 cm), and can include a selected pattern array of scarfing pins distributed along the outer surface of the scarfing roll core. For example, the scarfing elements may be arranged in rows that extend along the axial direction of the scarfing roll. In a particular arrangement the scarfing roll 34 can include approximately 8 rows of pins with approximately 0.5 inch (about 1.3 cm) spacing between individual pins. The scarfing pins can have a diameter of about 0.125 inch (0.32 cm), and a length of about 0.5–2.5 inch (about 1.3–6.4 cm). Additionally, the rows of scarfing elements may be distributed around the circumference of the scarfing roll at substantially, equally spaced intervals. The scarfing elements can be integrated with the scarfing roll by any operative attachment system, such as a formation from a common material stock, screwing, welding or the like, as well as combinations thereof. For example, the scarfing elements may be threaded and screwed into the outer surface of the scarfing roll core. To help accommodate the mounting and attachment of the scarfing elements, flat areas may be formed on the surface of the scarfing roll.

The scarfing roll 34 is operatively rotated by a suitable drive mechanism, such as an electrical motor. Any other operative drive mechanism may alternatively be employed. In the representatively shown configuration, the scarfing roll 34 can be rotated at any operative speed that is sufficient to provide the desired scarfing operation. For example, the rotational speed of the scarfing roll can be within the range of about 900–3600 RPM (revolutions per minute), or more, to provide desired levels of performance. In a particular arrangement the rotational speed of the scarfing roll can be about 1800 RPM.

In a desired arrangement, the scarfing roll 34 is operatively rotated in a direction such that when the scarfing pins contact the web, the scarfing pins are translated in a direction that is counter to the movement direction of the fibrous web 22. Alternatively, the scarfing roll 34 can be rotated such that when the pins are contacting the fibrous web, the scarfing pins are traveling in substantially the same direction as the movement direction of the fibrous web 22.

In the representatively shown configuration, the scarfing system can be arranged with the axis of rotation of the scarfing roll aligned substantially parallel with the axis of rotation of the forming drum. At the portion of the forming surface 42 that is most proximally adjacent the scarfing roll 34, a base reference line 64 can be aligned 90° to the line that joins the drum axis and the scarfing roll axis (e.g. FIG. 2). Accordingly, the base reference line 64 can be aligned substantially tangent to or otherwise generally parallel to the local movement direction of the fibrous web 22, as determined at the position of the scarfing roll 34. Additionally, a scarfing reference plane for the scarfing action can extend substantially parallel to the axial dimension of the scarfing roll and parallel to the base reference line. The reference plane of the scarfing action can substantially intersect the region where the scarfing elements (e.g. the scarfing pins of the scarfing roll) strike the initially formed fibrous web.

The scarfing roll 34 can rotate at a relatively high rate of speed to provide an operative scarfing motion. As representatively shown, the resulting scarfing motion can be in a direction that is substantially opposite to the movement direction of the formed fibrous web 22. This arrangement can generate an "explosive" impact when the scarfing pins (or other scarfing elements) contact the formed web 22. As the pins continue to move through the web material, most (but not necessarily all) of the scarfed and removed material can be projected forward along the movement direction of the scarfing pins. Generally stated, the forward movement of the scarfed material is caused by the momentum imparted to the scarfed material by the impulse applied by the moving scarfing pins. The movement of the scarfed material is distributed along a directional spectrum that begins substantially parallel to the local movement direction of the fibrous web, and substantially ends at an angle of about 60° away from this parallel. Accordingly, the movement of the scarfed material can have a projection angle within the range of about 0°–60°. Up to about 90% of the scarfed material can be thrown forward at a projection angle which is within the range of about 10°–40°. Some of the heavier materials, such as the particles of superabsorbent material, may however, be thrown at projection angles that are outside the range of about 0°–60°. Techniques for a more effective handling these heavier materials are described elsewhere in the present disclosure.

By distinctively configuring the discharge conduit 30, the invention can exploit the inertia and momentum imparted by the scarfing operation. The imparted momentum can be combined with a cooperating airflow that can be selectively directed through the scarfing housing to provide an increased capacity to move and transport a higher mass-rate of material from the scarfing housing. As a result, the technique of the invention can more effectively and more reliably generate the desired basis-weight distributions of web material along the longitudinal, lengthwise dimension of the scarfed web.

The discharge conduit 30 can have any operative configuration. For example, the cross-sectional shape of the discharge conduit may be circular, oval, rectangular, polygonal, or the like, as well as combinations thereof. In the illustrated arrangement, the discharge conduit is substantially straight. In alternative arrangements, the discharge conduit may optionally include a curved, bent or otherwise nonlinear configuration.

Figure 6:
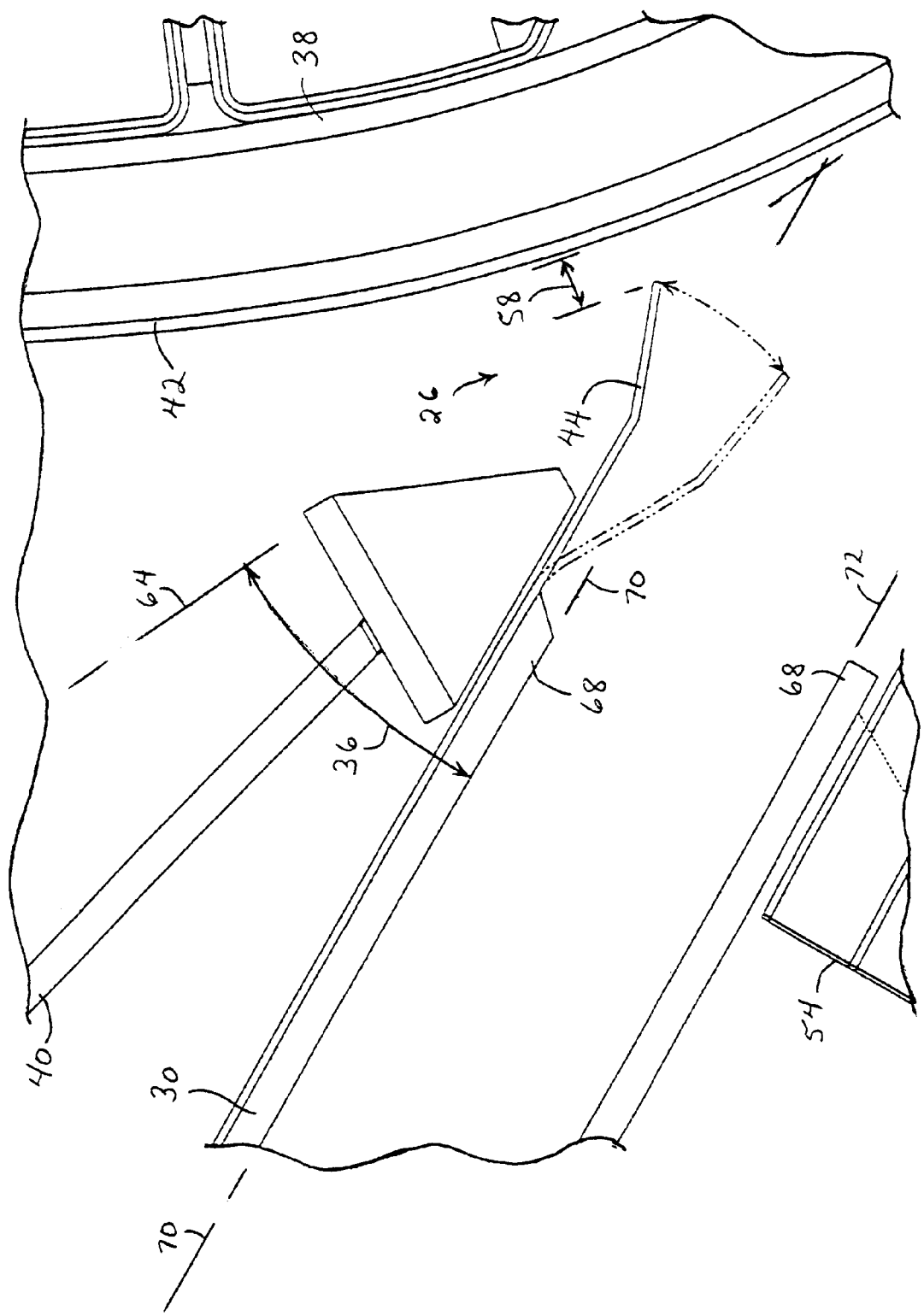
FIG. 6 shows an enlarged schematic, cross-sectional side view at the entrance of a discharge conduit employed with the present invention.

In a particular feature of the invention, at least an entry portion 68 of the discharge conduit 30 can have a selected alignment relative to the base reference line 64. With reference to FIG. 6, the entry portion 68 of the discharge conduit 30 provides a conduit leading-edge and a conduit trailing-edge. In the representatively shown arrangement the conduit leading-edge is positioned relatively closer to the forming surface 42, and the conduit trailing-edge is located relatively downstream from the conduit leading-edge, as determined with reference to the direction of rotation of the scarfing roll 34. A leading-edge line 70 is substantially parallel to the leading edge structure of the discharge conduit 30 at the entry portion 68 of the discharge conduit. As representatively shown, the angle between the base-reference line 64 and the conduit leading-edge line 70 is the conduit angle 36 of the discharge conduit.

For improved operation, the discharge conduit 30 can be configured with a selected conduit angle 36. In a particular feature, the conduit angle can be at least a minimum of about 10 degrees (10°). The conduit angle can alternatively be at least about 20°, and optionally, can be at least about 25° to provide improved performance. In other aspects, the conduit angle can be not more than a maximum of about 80°. The conduit angle can alternatively be not more than about 70°, and optionally, can be not more than about 50° to provide improved effectiveness. In a desired configuration, the conduit angle can be not more than about 60° to provide desired performance.

Due to operational issues, it can be inefficient to install the discharge conduit with a conduit angle of less than about 10°. At excessively large conduit angles, the removed material can be less efficiently directed into the discharge conduit. The transport of the scarfed material from the scarfing housing can then be excessively dependent on the airflows through the scarfing housing. Additionally, the mechanical advantage that can be derived by exploiting the impact momentum generated by the scarfing pins may be lost.

It has been desirable to substantially match the size of the entry opening in the entrance portion 26 of the scarfing housing 24 to the size of the incoming fibrous web. In particular, it has been desirable to maintain a substantially zero or relatively small gap between the distal edge of the damper member 44 and the topmost surface of the formed fibrous web that is entering the scarfing housing. This arrangement allows the damper member 44 to better provide the desired segregation between the scarfing housing 22 and the forming chamber 24. During the various conditions of the manufacturing operations, however, there can be significant and dramatic changes in the size of the formed fibrous web that is entering the scarfing housing. During ordinary, steady-state operating conditions, for example, the entering web can have a relatively smaller size. In particular, the entering web can have a relatively smaller thickness dimension. After a shut-down and start-up sequence, however, the entering web can have a significantly larger size, particularly a much larger thickness dimension. In conventional systems, the size of the entry opening has been substantially fixed at a size that has accommodated and substantially matched the size of the entering web that is encountered during steady-state conditions. As a result, such conventional designs have experienced disruptive jams in the forming chamber, and have suffered expensive equipment damage during start-up conditions when attempting to force a heavy, thick web out of the forming chamber and though the entry opening into the scarfing housing.

With conventional scarfing techniques, most of the scarfed material can be thrown back into the forming chamber instead of being transported through the discharge conduit. As a result of this kick-back of scarfed material, the scarfing system may tend to act as a plow. The kick-back and plowing effects have caused random changes in the magnitude of the scarfing load, and has caused random surges in the basis weight and thickness of the web being delivered to the scarfing roll. The kick-back and plowing effects have also caused undesired variability in the basis weight distributions along the length of the web.

A particular aspect of the invention can include a distinctive damper member 44. The damper 44 can more efficiently divide the forming chamber from the scarfing roll housing and can more effectively segregate the scarfed material in the scarfing housing 24 from the forming material in the forming chamber 22. The segregation can help ensure a more consistent removal of scarfed material out from the scarfing housing. In a particular feature, the segregation can more effectively reduce a kicking-back of scarfed material from the scarfing housing 24 and into the forming chamber 22 through the entrance opening of the scarfing housing. A large proportion of the scarfed material can be propelled toward the location of the damper member, and the configuration of the damper member can help provide a more effective directing of the scarfed material away from the forming chamber. Additionally, the configuration of the damper member can more effectively direct the scarfed material into and through the discharge conduit.

In another aspect, the damper member can also more reliably counteract an undesired influx of air-entrained forming material from the forming chamber 22 into the scarfing housing 24. A pressure differential between the forming chamber and the scarfing housing can create a flow pattern out of the forming chamber and into a scarfing housing. For example, the velocity of the airflow into the discharge conduit 30 can contribute to the pressure differential since the air velocity in the forming chamber can differ from the airflow velocity into the discharge conduit. The resulting pressure differential can draw air-entrained material from the forming chamber into the scarfing housing. If excessive, airborne forming material is carried into the scarfing housing, the extra material can subsequently flow up the discharge conduit 30 and add unnecessary recycle to the manufacturing process. Conventional arrangements of forming chamber and scarfing housing, however, have not adequately prevented the undesired fiber/particle migration from the forming chamber 22 into the discharge conduit 30.

With the present invention, however, the more effective segregation of material between the forming chamber and the scarfing housing can improve the efficiency of the scarfing operation and can more reliably produce the desired basis weight distributions along the lengthwise dimension of the fibrous web.

Figure 7:
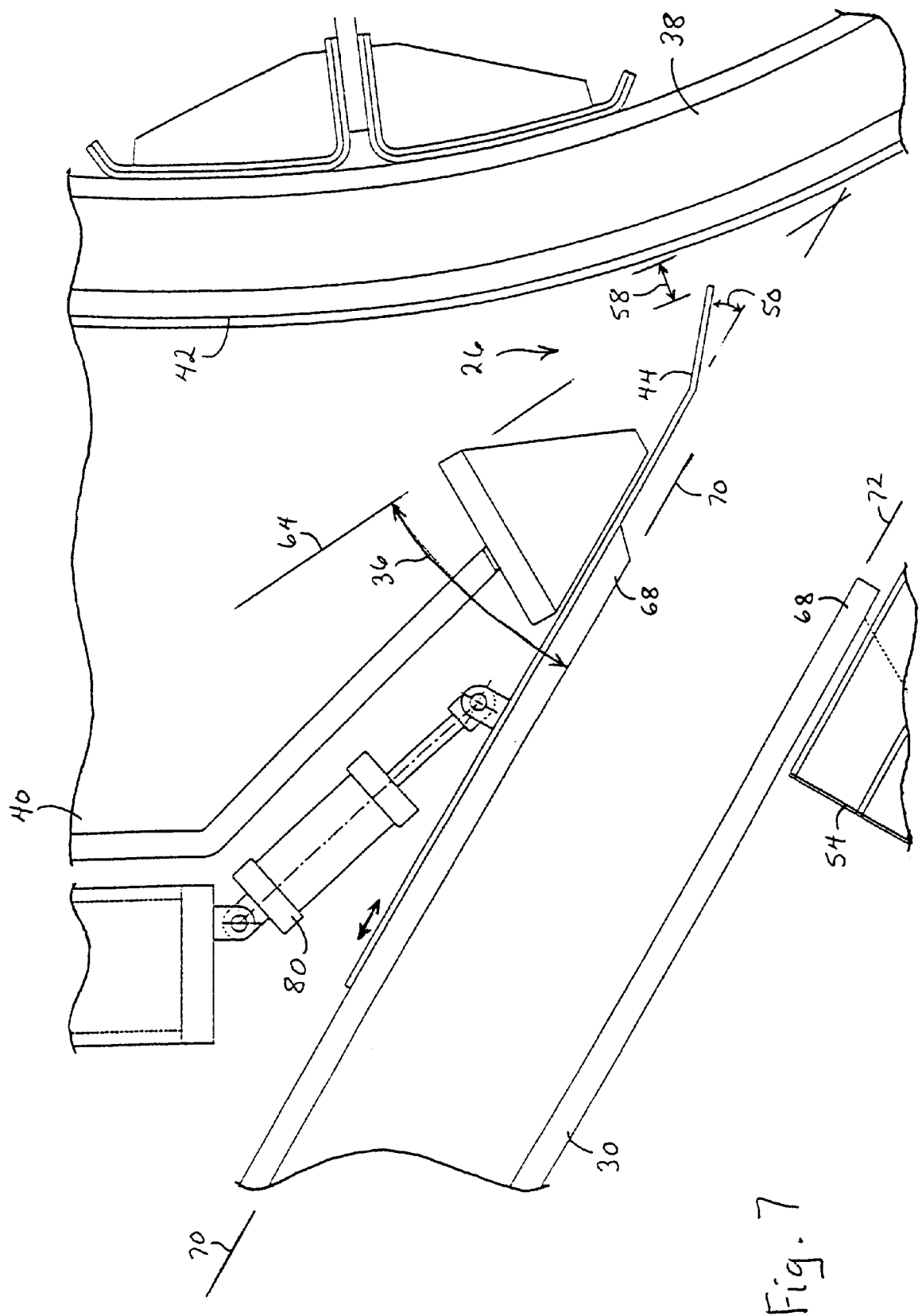
FIG. 7 shows an enlarged schematic, cross-sectional side view an alternative configuration having a movable damper member operatively connected to a cooperating actuator.
Figure 8:
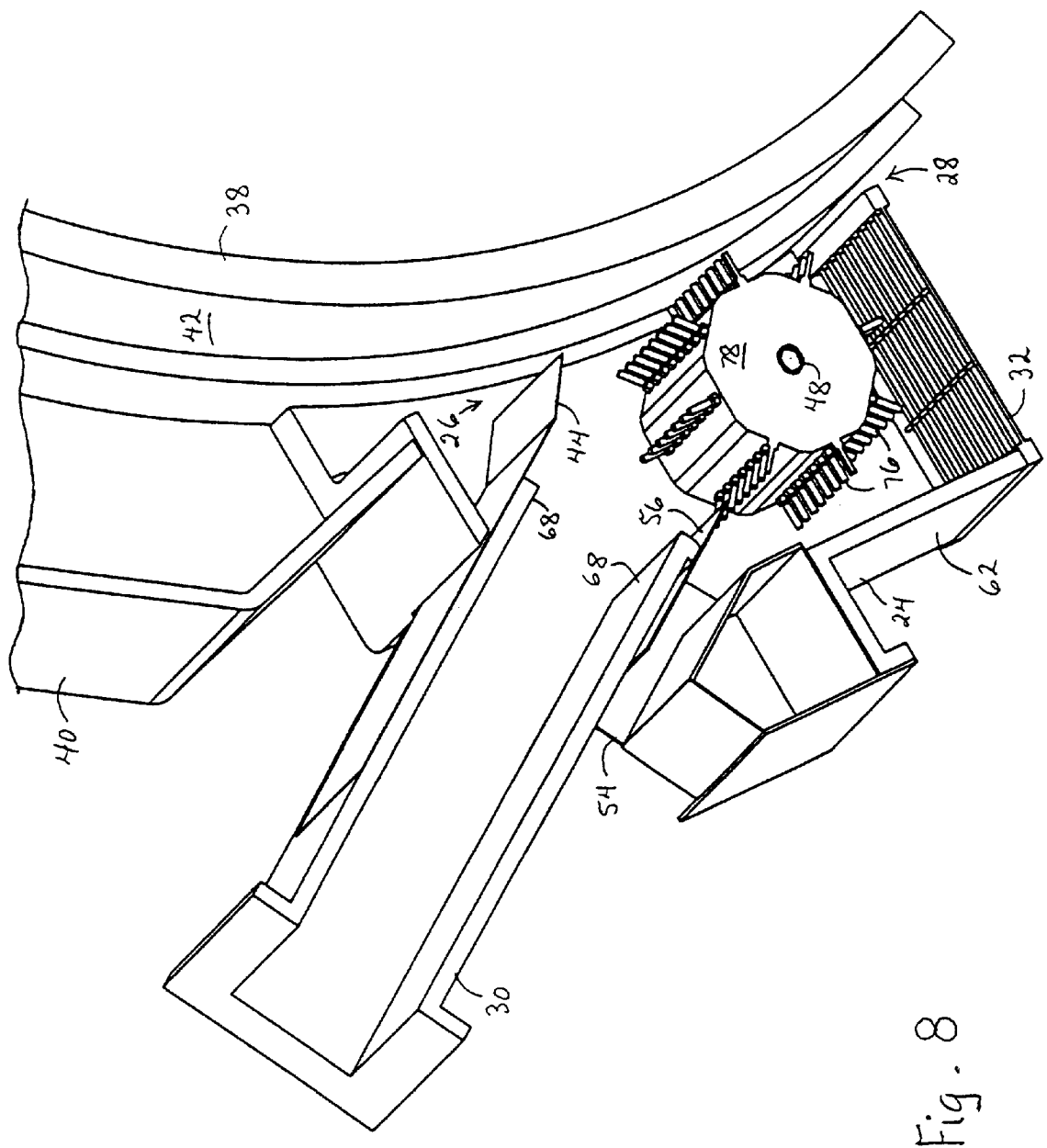
FIG. 8 shows perspective view of a representative apparatus and method of the invention.

With reference to FIGS. 1, 6 and 7, a movable damper 44 can be operatively positioned at the web entrance portion 26 of the scarfing housing 24. In a particular aspect, the movable damper 44 is capable of changing a size of an entrance opening in the web entrance portion 28 of the scarfing housing 24. In a further aspect the movable damper 44 can be capable of changing the size of the entrance opening in the web entrance portion 26 of the scarfing housing in correspondence in a change in size of the fibrous web 22. In particular, the movable damper 44 can be capable of changing the size of the entrance opening in correspondence with a change in thickness of the fibrous web 22. Accordingly, the movable damper can deflect or otherwise selectively move to more effectively allow the thick web into the scarfing housing.

In particular feature, the movable damper 44 can resiliently flex to thereby change the size of the entrance opening in the entrance portion 26 of the scarfing housing 24. In a further aspect, the movable damper 44 can resiliently flex with a selected spring force to thereby change the size of the entrance opening. For example, the damper may be a sheet or plate member constructed with spring steel.

In optional configurations, the invention can further include an actuator 80 which is operatively connected and configured to displace the movable damper 44 to thereby change the size of the entrance opening in the web entrance portion 26 of the scarfing housing 24. Various types of suitable actuators are well known in the art. Such actuators can be configured to bend, pivot, slide or otherwise deflect the damper 44 to thereby change the size of the entrance opening into the scarfing housing. In a particular arrangement, the actuator can be connected and configured to swing the movable damper about a selected rotational axis to thereby change the size of the entrance opening. In other arrangements, the actuator may slide or otherwise advance or retract the position of the damper 44 to adjust the entrance opening size.

The damper member 44 can be made of any operative material, such as metal, synthetic polymer material, composite material or the like, as well as combinations thereof. In the representatively shown configuration, the damper member 44 can be constructed with spring steel. The damper member can, for example, be a plate member, and the plate can have a plate thickness of about 0.025 inch (0.06 cm). The plate thickness can alternatively be as thick as about 0.125 inches, and optionally, can be as thin as about 0.010 inch (0.025 cm). Additionally, the plate member can have an effective length of about 4.5 inch (about 11.4 cm). Where the movable damper member is configured to be pivotable, the effective length of the damper member is the length that is available for flexing or otherwise swinging to increase or decrease the size of the entrance opening. It should be readily apparent that the spring force provided by the damper plate can depend on the particular dimensions and composition of the plate member. Accordingly, the adjustment of such factors to arrive at an operative spring force would be well known to persons of ordinary skill.

In its various configurations, the movable damper can deflect to temporarily increase the size of the entry opening into the scarfing housing and more efficiently allow the heavy start-up web out into the scarfing housing for the desired scarfing operation. The incorporation of the movable damper can reduce process delay and reduce equipment damage. The movable damper member 44 can also more effectively and more reliably keep the web-forming material in the forming chamber 22, and keep the scarfed material in the scarfing housing 24.

The movable damper can be located at the entrance portion of the scarfing housing, and can be arranged to extend below a leading-edge portion of the discharge conduit, as representatively shown in FIGS. 6 and 7. The movable damper 44 can be configured to provide a selected damper gap 58 between the terminal, distal free edge of the movable damper 44 and the operative conveying surface of the transporter. In the representatively shown configuration, the damper gap can be maintained between the terminal, distal edge of the movable damper and the forming surface 42. The damper gap can be about 1.75 inch (about 4.4 cm). In alternative arrangements, the damper gap can be as small as about 0.25 inch (about 0.64 cm), or as large as about 3 inch (about 7.6 cm).

To reduce the movement of material between the forming chamber 22 and the scarfing housing 24 and to allow a reliable entrance of heavy, thick webs into the scarfing housing without disruptive jams, the damper member 44 can be cooperatively configured to exploit the geometric shape of the scarfing housing. In a particular feature, a decreasing-size cone or wedge shape can be presented to advancing web 22 as the web enters the scarfing housing. The decreasing wedge shape can facilitate a smooth entry of the web into the scarfing chamber, and can facilitate any deflection of the damper member 44 that may be imparted to the damper member by a large or oversize web. In a particular feature, the damper member 44 can provide a variable, pivoting or swinging deflection or movement to thereby pass a web of varying thickness while continually maintaining a relatively small damper gap between the distal edge of the damper member and the top surface of the fibrous web 22. The damper member 44 can be configured to provide a damper deflection of at least a minimum of about 10°. The damper deflection can alternatively be at least about 20°, and optionally can be up to about 30°, or more, to provided an improved ability to pass thick, high basis weight webs.

In a desired feature, the movable damper 44 can deflect or otherwise move to provide a selected change in the damper gap 58. The change in the damper gap can, for example, be at least a minimum of about 1 cm. The damper gap can alternatively be at least about 2 cm, and optionally, can be at least about 3 cm to provide improved performance. In other aspects, the damper gap can be not more than a maximum of about 9 cm. The damper gap can alternatively be not more than about 7 cm, and optionally, can be not more than about 5 cm to provide improved effectiveness.

The change in the damper gap 58 is the distance (as determined along a line that is perpendicular to the base reference line 64) that is traversed when the damper 44 is displaced from its position of closest approach to the forming surface, to another location that is away from such position of closest approach.

In another feature, the plate member can have a selected shape along its lengthwise direction, and in a particular aspect, the shape can include a selected bend angle 50. The bend angle may have an abrupt, sharp configuration with a relatively distinct apex. Alternatively, the bend angle may be gradual and more curved. The bend angle is desirably arranged to be generally convex in the direction toward the forming chamber. Where the bend angle has a relatively sharp apex, the apex can be pointed away from the forming chamber (e.g. FIGS. 6 and 7). Where the bend angle is more curved, the convex side of the curve can be pointed away from the forming chamber. In a particular configuration, for example, the bend angle can be about 20°. The bent section at the distal end portion of the damper member can have any operative length. In a particular arrangement, for example, the bent section can have a length of about 2 inch (about 5 cm). Accordingly, the method and apparatus of the invention can be configured so that substantially no suspended forming material will be drawn from the forming chamber into the scarfing housing.

The bend angle in the damper member can help to counteract the impact of any aerodynamic "lifting" force that may tend to undesirably move the distal end of the damper member away from its intended position that is closely proximate the surface of the fibrous web. In the absence of the bend angle in the damper member, the damper member may undesirably deflect as much as 0.38 inch (about 1 cm) towards the scarfing roll during the scarfing operation. The air flowing through the discharge conduit and past the damper member can generate the "lift" force that causes the undesired deflection. The angled kink or bend that is provided in the bent damper member, however, can present a modified surface that can operatively induce a counteraction against the lift force. As a result, the undesired lift-deflection can be reduced, and the desired positioning of the distal end of the damper member can be better maintained. In a particular feature, the undesired lift-deflection can be limited to not more than a maximum of about 0.12 inches (about 0.3 cm).

A further aspect of the invention can provide an improved "peel rate" of the scarfed material. The peel rate is a function of the forward speed and velocity of the web as it is transported on the forming drum. This forward web speed and velocity can determine the minimum functional speed and velocity that should be effectively imparted to the material that is scarfed and removed from the fibrous web.

The selected transporter, such as provided by the rotatable forming drum 38 and its associated forming surface 42, can convey the fibrous web 22 through the scarfing housing 24 at a selected web transport speed. In a particular aspect, the web transport speed can be at least a minimum of about 3 meters per second (about 590 ft/min). The web transport speed can alternatively be at least about 5 m/sec (about 984 ft/min), and optionally, can be at least about 7 m/sec (about 1378 ft/min) to provide improved performance. In other aspects, the web transport speed can be up to a maximum of about 17 m/sec (about 3400 ft/min), or more. The web transport speed can alternatively be up to about 14 m/sec (about 2800 ft/min), and optionally, can be up to about 11 m/sec (about 2200 ft/min) to provide improved effectiveness. In a particular arrangement, the speed of the moving web 22 can be about 5.1 m/sec (about 1000 ft/min).

As the scarfing roll pins impact the web, velocity and momentum are imparted to the fibers and particles of scarfed material pad. It is important to transport the scarfed material away from the web at a transport rate that is at least equal to the rate at which the scarfed material is being driven and separated from the web. In a particular aspect, the transport mechanism can include a housing airflow through the scarfing housing. In another feature, the housing airflow can be configured to have a selected volume-rate of flow. In a further feature, the method and apparatus of the invention can be configured to provide a selected take-away airflow speed within the scarfing housing 24. In a particular aspect, the take-away air flow speed can be configured to be greater than the web transport speed.

The airflow rate or speed can be calculated with respect to a selected, dimensional plane of the invention. In a particular aspect, the selected dimensional plane can be a plane in the scarfing housing, and can be identified by determining a planar, cross-sectional area that intersects the regional location at which the scarfing pins make their closest approach to the forming surface, and provides the smallest area through which flows substantially all of the air that enters the scarfing housing. This cross-sectional area can be referred to as a peel-area. Any operative arrangement of appointed inlets and openings may be employed to provide the corresponding, total entering air flow. The representatively shown arrangement of the invention, for example, can be configured to have substantially all of the entering air pass through the inlet chimney 54 and the primary airflow inlet 32.

It should be readily apparent that the planar area employed to determine the desired airflow speed in the scarfing housing can depend upon the structural shape chosen for the scarfing housing, and that any operative housing shape may be employed with the present invention. As representatively shown, the appropriate peel-area can be generally rectangular, and can measure approximately 7.84 inch×8.75 inch (about 20 cm×22 cm). The 8.75 inch dimension can be substantially parallel to the rotational axis of the scarfing roll 34, and the 7.84 inch dimension can be perpendicular to the rotational axis of the scarfing roll.

Additionally, the 7.84 dimension may vary by ±0.75 inch. The airspeed for the illustrated arrangement can be determined with respect to this peel-area.

In a particular aspect, the minimum airspeed can be at least the speed at which the web is being transported through the scarfing housing (web speed). In another aspect, the housing airspeed can be at least about 1.25 times or 2 times the web speed through the scarfing housing 24. In a further aspect, the housing airspeed can be up to about 3 times the web speed, or more. If the housing airspeed is too low, the scarfed material may not be adequately transported away from the web 22, and may not be adequately directed into the discharge conduit 30. If the airflow speed through the scarfing housing 24 is too high, aerodynamic forces may lift the fibrous web 22 away from the transport surface (e.g. forming surface 42). This web-lifting effect can cause plugging or jamming within the scarfing housing, and can create excessive variations in the final basis weight of the scarfed fibrous web 22.

The desired airflow volume-rate through the scarfing housing 24 can, for example, be expressed in any convenient units of volume per time. This rate can be a minimum of about 750 ft$^3$/min (about 21 m$^3$/min, and a maximum of about 1200 ft$^3$/min (34 m$^3$/min).

At an airflow volume-rate of 750 ft$^3$/min (about 21 m$^3$/min), the take-away airspeed through the illustrated peel-area can be about 1576 ft/min (about 480 m/min). At 1200 ft$^3$/min (about 34 m$^3$/min), the take-away airspeed through the illustrated peel-area would be about 2521 ft/min (about 768 m/min). If the web speed was functioning at one times the housing airspeed, the web speed could be within the range of about 1576–2521 ft/min (about 480–768 m/min). For a housing airspeed of 3 times the web speed, the web speed could be within the range of about 525–840 ft/min (about 160–256 m/min).

In a further aspect, the method and apparatus of the invention can be configured to provide an airflow speed through the discharge conduit 30 which is at least a minimum of about 3,000 ft/min (about 914 m/min). The minimum airflow speed is important for keeping the removed fibrous material suspended in the conveying air stream that carries the fibers through the discharge conduit 30. If the air speed is too low, the fibrous material can excessively settle out from the conveying air stream.

As mentioned in the present disclosure, any operative device can be used to generate a sufficient force, such as provided by a pressure differential, to impart the desired airflow volume-rate and/or airspeed through the various components or process operations employed by the present invention. Such devices are well known in the art, and can, for example, include air pumps, fans, blowers or the like, as well as combinations thereof.

When relatively large amounts of fibrous material are removed from the fibrous web 22 during the scarfing operation, the removed fibrous material may travel around the circumference of the scarfing roll 34. If the removed, scarfed fiber material is allowed to circulate or otherwise move circumferentially around the scarfing roll, the scarfed material can undesirably be re-deposited onto the previously-scarfed web. Additionally, the scarfed material can collect at the bottom of the scarfing housing. As a result, the fugitive fiber can excessively reduce and may eventually block the desired airflow into the scarfing housing.

In a further aspect of the invention, the scarfing housing can include configurations that reduce or substantially prevent the undesired rotational flow of fiber material around the circumference of the scarfing roll. With reference to FIGS. 2 through 5, the scarfing housing can include an inlet chimney 54, and the inlet chimney can be configured to help force the scarfed material to ascend the discharge conduit 30. In a particular feature, the inlet chimney can direct a flow of stripper air towards the scarfing pins. The stripper airflow can help to separate any scarfed material that may clinging to the scarfing pins and direct the scarfed material into the discharge conduit 30.

The inlet chimney 54 can be configured to provide a selected, inward curtain of airflow. The airflow curtain can substantially block or otherwise hinder the undesired circulation-flow of fiber material around the periphery of the scarfing roll. In a particular feature, this curtain airflow can be up to approximately 50% of the total airflow entering the scarfing housing. The curtain airflow can alternatively be at least a minimum of about 15% of the total airflow into the scarfing housing, and optionally, may be up to about 35% of the total airflow into the scarfing housing.

In another feature, the inlet chimney 54 can be positioned generally adjacent to and relatively downstream from the discharge conduit 30. Within the scarfing housing 24, the relatively downstream direction is determined with respect to the direction of rotation of the scarfing roll 34. The inlet chimney 54 can be suitably adjusted to provide an operative, stripper air stream directed towards the scarfing roll 34. In particular arrangements, the stripper air stream can be powered or otherwise induced by the discharge fan 66, and the stripper air stream can be directed towards the pins of the scarfing roll. The resulting airflow through the inlet chimney 54 and into the scarfing housing 24 can provide an operative air-curtain that can effectively block or otherwise impede an excessive circulation movement of fibrous material around the circumference of the scarfing roll 34.

Figure 2:
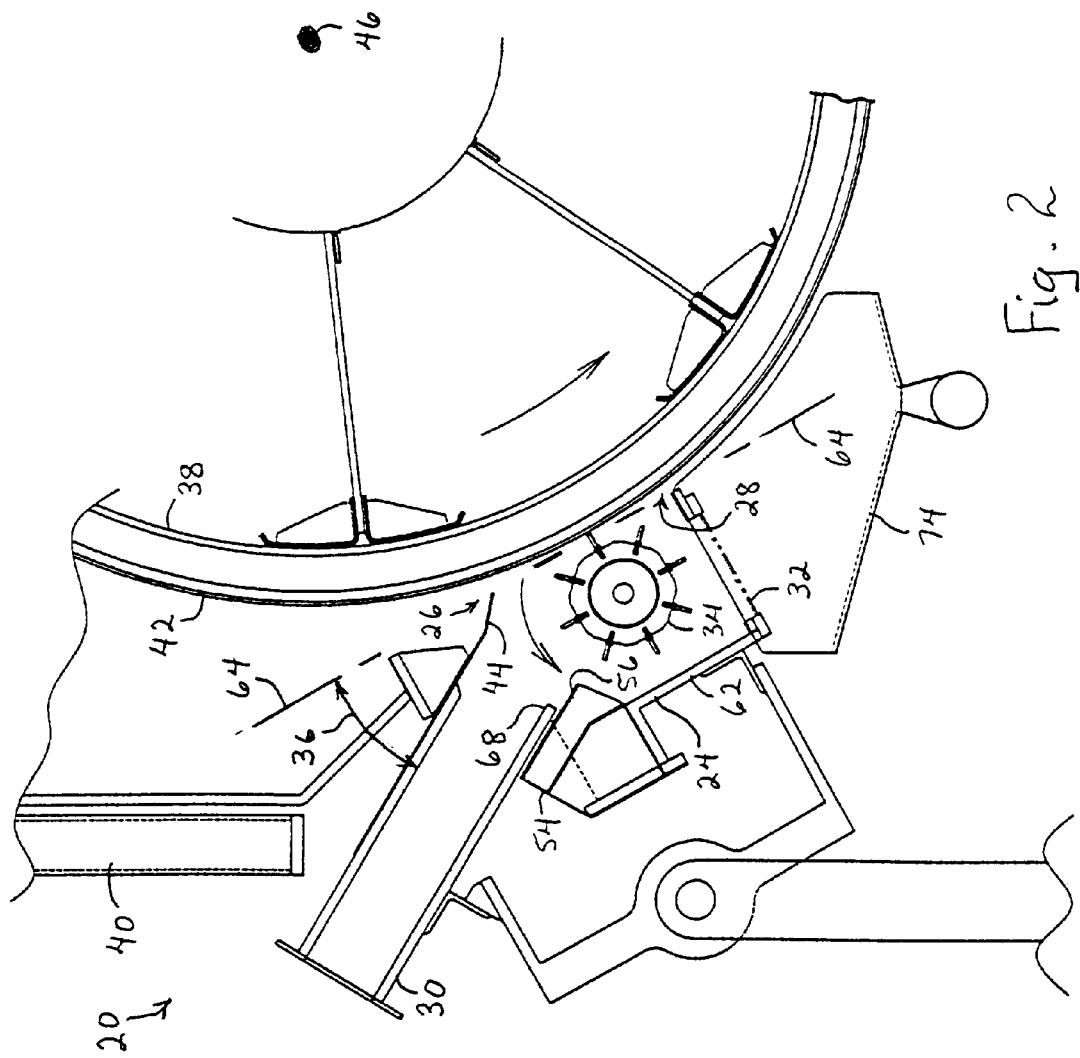
FIG. 2 shows a schematic, cross-sectional side view of a scarfing operation that employs a representative method and apparatus of the present invention.
Figure 2A:
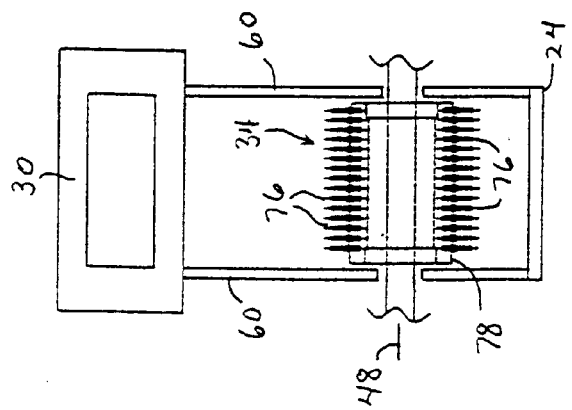
FIG. 2A shows a partially sectioned, end view of the scarfing system that is representatively shown in FIG. 2.
Figure 3:
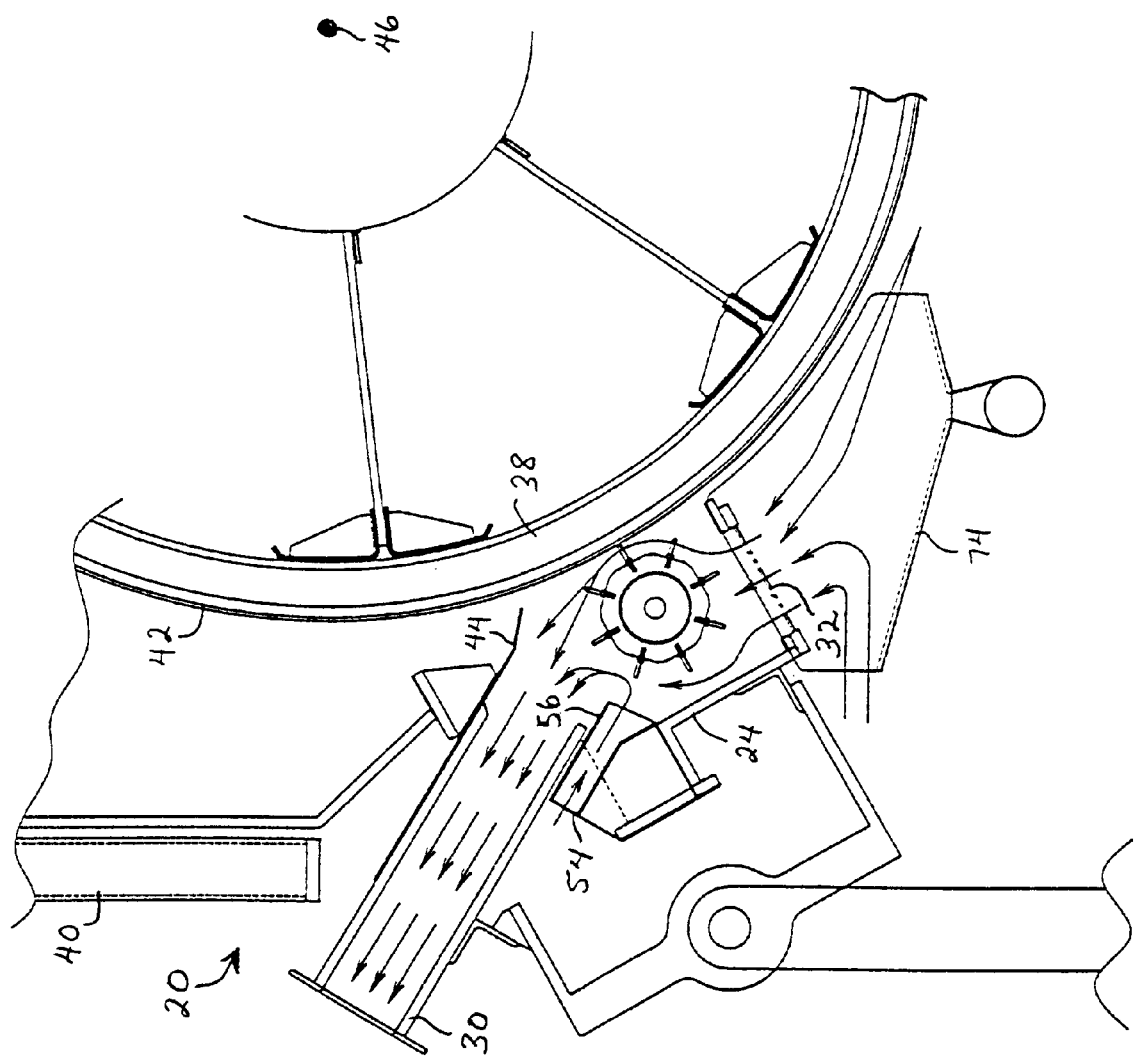
FIG. 3 shows a schematic, cross-sectional side view which shows representative airflows through the configuration of the invention illustrated in FIG. 2.

With reference to FIGS. 2 and 4, another feature of the method and apparatus can provide at least one insert member 56 which can be configured to operatively impede a movement of particulate material removed from the fibrous web 22 during the scarfing of the fibrous web. In a further aspect, the insert member can be installed in or at the inlet chimney. The particulate material may, for example, include particles of superabsorbent material. Typically, the particulate material can be heavier with relatively high mass. As a result, the airflow through the scarfing housing 24 is ordinarily less effective at directing the heavier particulate material into and through the discharge conduit 30. The superabsorbent material can be mechanically propelled off the scarfing pins, and can ricochet within the housing. The stripper airflow alone, however, may not adequately overcome the momentum of the superabsorbent particles. As a result, the particles can fling up to a full 360° around the scarfing roll, and can bounce or otherwise fall out of the scarfing housing. Additional systems may be employed to capture and contain the fugitive particles, and the captured particles may be reintroduced into the web forming system.

Configurations of the invention that incorporate the insert member 56, however, can effectively block or otherwise adjust the motion of the particulate material that may be tending to circulate around the scarfing roll, and can more effectively redirect the particulate material into the discharge conduit 30. The insert member 56 can provide a mechanical blocking of the particles, and can substantially halt or operatively reduce the amount of particles that are undesirably expelled from the scarfing housing through various inlet openings.

Figure 5:
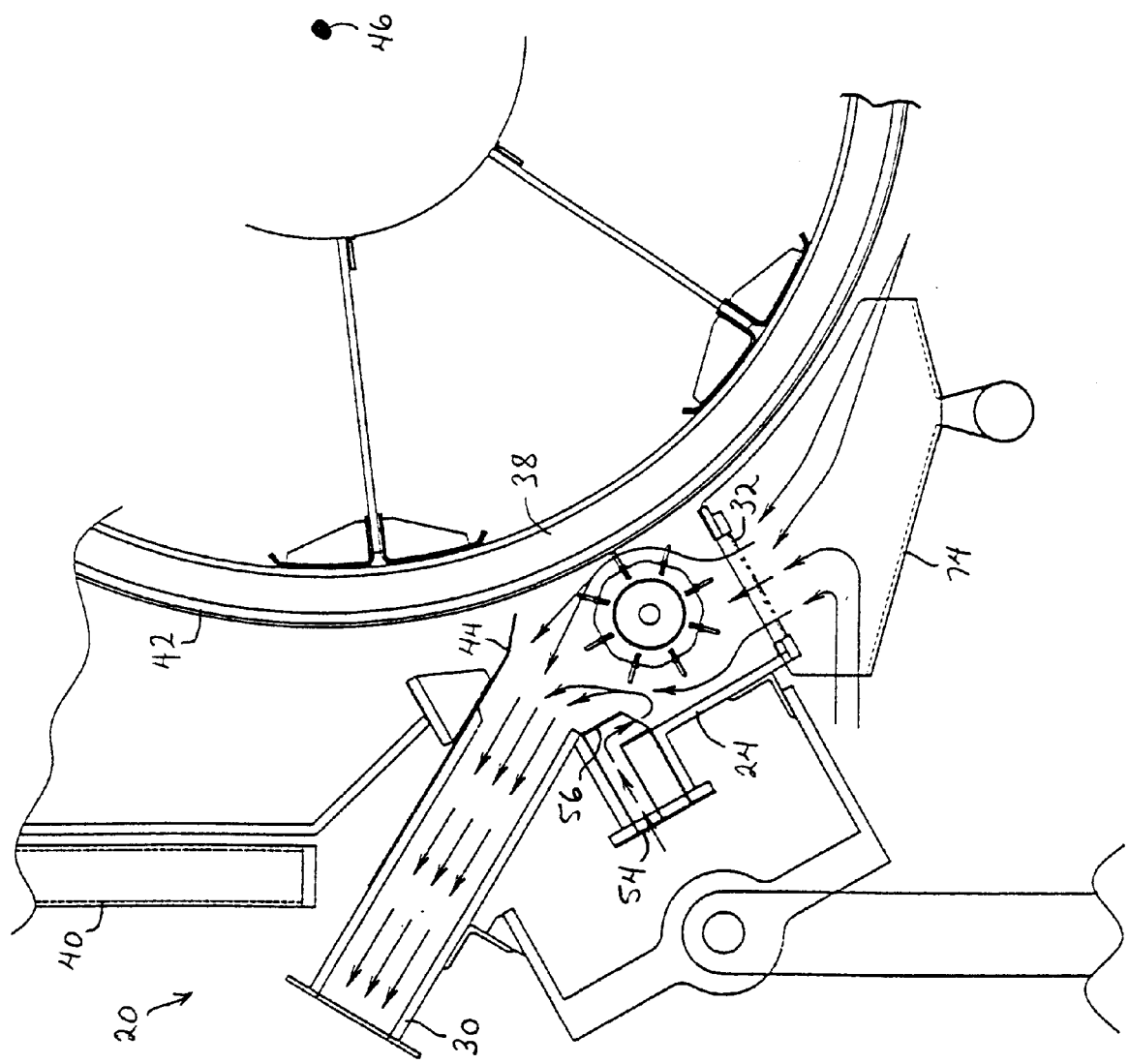
FIG. 5 shows a schematic, cross-sectional side view which shows representative airflows through the configuration of the invention illustrated in FIG. 4.

With reference to FIGS. 2 and 5, the insert member 56 can be positioned generally adjacent to and relatively downstream from the discharge conduit 30 (as can be determined when moving along the rotational direction of the scarfing roll). In a particular feature, the inlet chimney 54 can be suitably aligned and configured to substantially block or otherwise inhibit a movement of particulate material out from the scarfing housing 24 through the inlet chimney 54. For example, the inlet chimney 54 can be arranged with a downward slant with the relatively inside opening of the inlet chimney positioned lower than the outside opening of the inlet chimney. Alternatively, the inlet chimney can be curved, angled or otherwise bent to include a hook-shape, as representatively shown in FIGS. 4 and 5.

Various attachments and securements may be employed in the constructions of the method and apparatus of the invention, it should be readily apparent that any conventional attachment or securement technique may be employed. Such techniques may, for example, include adhesives, welds, screws, bolts, nuts, rivets, pins, latches, clamps or the like, as well as combinations thereof.

Similarly, it should be readily apparent that any conventional material may be employed to construct the various components incorporated into the method and apparatus of the invention. Such materials can include synthetic polymers, fiberglass-resin composites, carbon fiber-resin composites, metallic composites, ceramic composites, and the like, as well as combinations thereof. The materials are typically selected to provide desired levels of strength, durability, ease of manufacture, and ease of maintenance.

Although various illustrative and representative configurations have been described in detail herein, it is to be appreciated that other variants, modifications and arrangements are possible. All of such variations, modifications and arrangements are to be considered as being within the scope of the present invention.

What is claimed:

1. An apparatus for scarfing a fibrous web, said apparatus comprising:
    a scarfing housing which has a web entrance portion, a web exit portion, an airflow inlet, and a discharge conduit;
    and a rotatable scarfing roll located in said scarfing housing; wherein
    said discharge conduit is configured with a conduit angle which is not more than a maximum of about 80°.

2. An apparatus as recited in claim 1, wherein said discharge conduit is configured with a conduit angle which is at least a minimum of about 10°.

3. An apparatus as recited in claim 1, further including a movable damper which is operatively positioned at said web entrance portion of said scarfing housing and is capable of changing a size of an entrance opening in said web entrance portion of the scarfing housing.

4. An apparatus as recited in claim 3, wherein said movable damper is shaped to resist an excessive deflecting of said damper away from said fibrous web.

5. An apparatus as recited in claim 4, wherein
    said apparatus further includes a transporter for conveying said fibrous web through said scarfing housing, and
    said movable damper is shaped to resist an excessive deflecting of said damper away from said transporter.

6. An apparatus as recited in claim 3, wherein said movable damper is capable of changing the size of said web entrance portion of the scarfing housing in correspondence with a change in size of said fibrous web.

7. An apparatus as recited in claim 3, wherein said movable damper is capable of resiliently flexing to thereby change the size of the entrance opening in said web entrance portion of the scarfing housing.

8. An apparatus as recited in claim 3, wherein said movable damper is capable of resiliently flexing with a spring force to thereby change the size of the entrance opening in said web entrance portion of the scarfing housing.

9. An apparatus as recited in claim 3, further including an actuator which is connected and configured to displace said movable damper to thereby change the size of the entrance opening in said web entrance portion of the scarfing housing.

10. An apparatus as recited in claim 9, wherein said actuator which is connected and configured to pivotably displace said movable damper to thereby change the size of the entrance opening in said web entrance portion of the scarfing housing.

11. An apparatus as recited in claim 3, wherein said movable damper is capable of providing a change in a damper gap of at least about 1 cm.

12. An apparatus as recited in claim 1, wherein
    said apparatus further includes a transporter for conveying said fibrous web through said scarfing housing at a web transport speed;
    said apparatus is configured to provide a take-away airflow speed within said scarfing housing; and
    said take-away airflow speed is configured to be greater than said web transport speed.

13. An apparatus as recited in claim 1, wherein said airflow inlet includes an inlet chimney portion configured to provide a stripper airflow towards said scarfing roll.

14. An apparatus as recited in claim 13, further including at least one insert member which operatively impedes a movement of particulate material removed from said fibrous web during said scarfing of the fibrous web.

15. A method for scarfing a fibrous web, said method including
    a providing of a scarfing housing which has a web entrance portion, a web exit portion, an airflow inlet, and a discharge conduit;
    a locating of a rotatable scarfing roll in said scarfing housing; and
    a configuring of said discharge conduit with a conduit angle which is not more than about 80°.

16. A method as recited in claim 15, further including a configuring of said discharge conduit with a conduit angle which is at least about 10°.

17. A method as recited in claim 15, further including an operatively positioning of a movable damper at said web entrance portion of said scarfing housing, said movable damper capable of changing a size of said web entrance portion of the scarfing housing.

18. A method as recited in claim 15, further including
    a providing of a transporter for conveying said fibrous web through said scarfing housing at a web transport speed; and
    a providing of a take-away airflow speed within said scarfing housing; said take-away airflow speed configured to be greater than said web transport speed.

19. A method as recited in claim 15, further including a configuring of said airflow inlet to include an inlet chimney portion which provides a stripper airflow towards said scarfing roll.

20. A method as recited in claim 15, further including a configuring of at least one insert member to operatively impede a movement of particulate material removed from said fibrous web during said scarfing of the fibrous web.

* * * * *